US00PP31531P2

(12) United States Plant Patent
Wood

(10) Patent No.: US PP31,531 P2
(45) Date of Patent: Mar. 10, 2020

(54) ***FORSYTHA* PLANT NAMED 'SMFXGP'**

(50) Latin Name: *Forsythia hybrida*
Varietal Denomination: SMFXGP

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/350,287

(22) Filed: Oct. 25, 2018

(51) Int. Cl.
*A01H 5/02* (2018.01)
*A01H 6/00* (2018.01)

(52) U.S. Cl.
USPC ..... Plt./230
CPC ..... *A01H 6/00* (2018.05)

(58) Field of Classification Search
USPC ..... Plt./230
See application file for complete search history.

*Primary Examiner* — Anne Marie Grunberg
(74) *Attorney, Agent, or Firm* — Cassandra Bright

(57) ABSTRACT

A new and distinct cultivar of *Forsythia* plant named 'SMFXGP' is disclosed, characterized by abundant flowering and compact plant size. The new variety is a *Forsythia*, normally produced as an outdoor garden plant.

3 Drawing Sheets

Latin name of the genus and species: *Forsythia hybrida*. Variety denomination: 'SMFXGP'.

BACKGROUND OF THE INVENTION

The new *Forsythia* cultivar is a product of a planned open pollination breeding program conducted by the inventor, Timothy Wood, in a poly-greenhouse in Grand Haven, Mich. The objective of the breeding program was to produce a new *Forsythia* variety that is more compact, with more abundant flowers. The cross resulting in this new variety was made in 2008.

The seed parent is the *Forsythia* x *intermedia* 'Courdijau', U.S. Plant Pat. No. 13,050. The pollen parent is unknown. The new variety was identified as a potentially interesting selection in 2012 at a poly-greenhouse in Grand Haven, Mich.

Asexual reproduction of the new cultivar 'SMFXGP' by softwood cuttings was first performed in 2012, at a poly-greenhouse in Grand Haven, Mich. Subsequent propagation has shown that the unique features of this cultivar are stable and reproduced true to type in five successive generations.

SUMMARY OF THE INVENTION

The cultivar 'SMFXGP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMFXGP'. These characteristics in combination distinguish 'SMFXGP' as a new and distinct *Forsythia* cultivar;

1. More abundant flowers.
2. Compact, sturdy plant.
3. Freely branching, upward and rounded plant.

PARENT COMPARISON

Plants of the new cultivar 'SMFXGP' are similar to plants of the seed parent in most horticultural characteristics; however, plants of the new cultivar 'SMFXGP' differ in the following;

1. New cultivar is more compact, whereas the parent is larger.
2. New variety's flowers are more abundant; Seed parent has fewer flowers per lateral branch.
3. Both the new variety and parent have yellow flowers.

COMMERCIAL COMPARISON

Plants of the new cultivar 'SMFXGP' can be compared to the commercial variety *Forsythia* 'Mindor', U.S. Plant Pat. No. 19,321. These varieties are similar in most horticultural characteristics, however 'SMFXGP' differs in the following;

1. New cultivar is more compact; this comparator is branchy, les compact.
2. New cultivar has more flowers per lateral branch than its comparator.
3. Both the new cultivar and comparator have yellow flowers.

BRIEF DESCRIPTION OF THE PHOTOGRAPHS

The accompanying photograph in FIG. 1 illustrates in full color a typical flowering plant of 'SMFXGP' grown outdoors.

Figure 1:
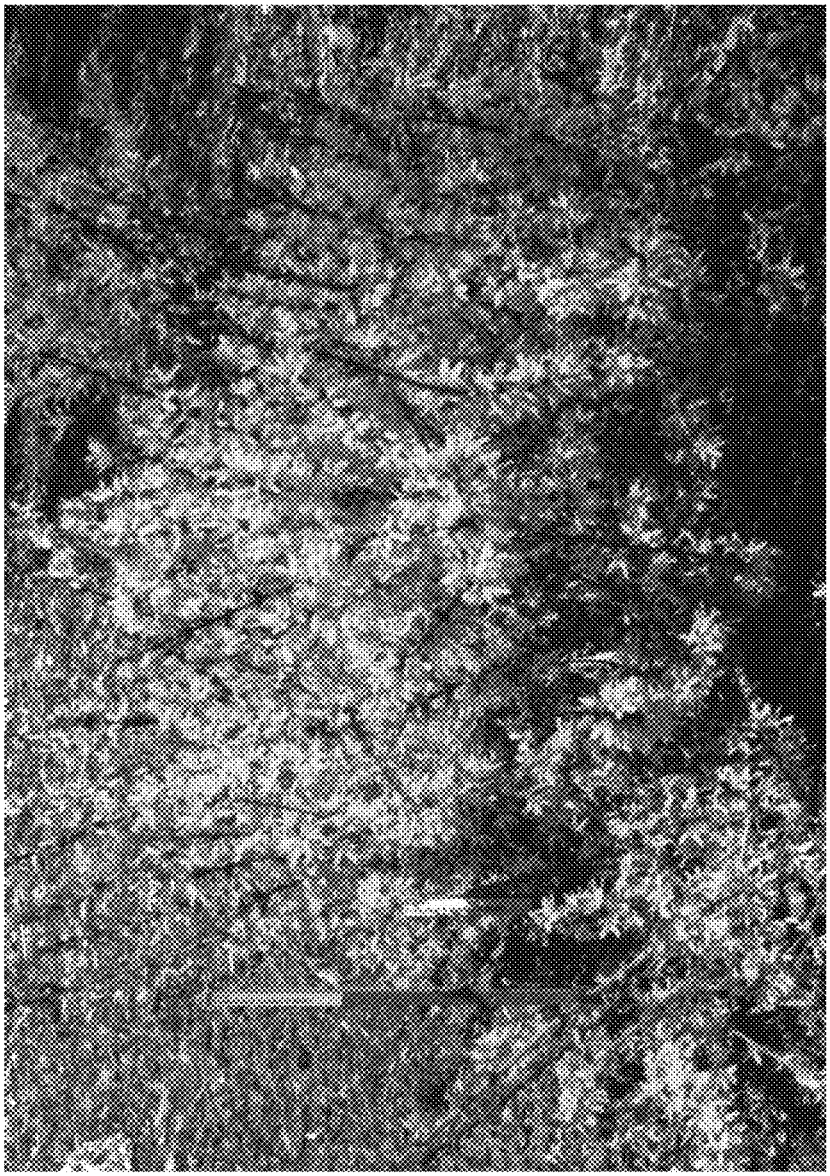
Figure 2:
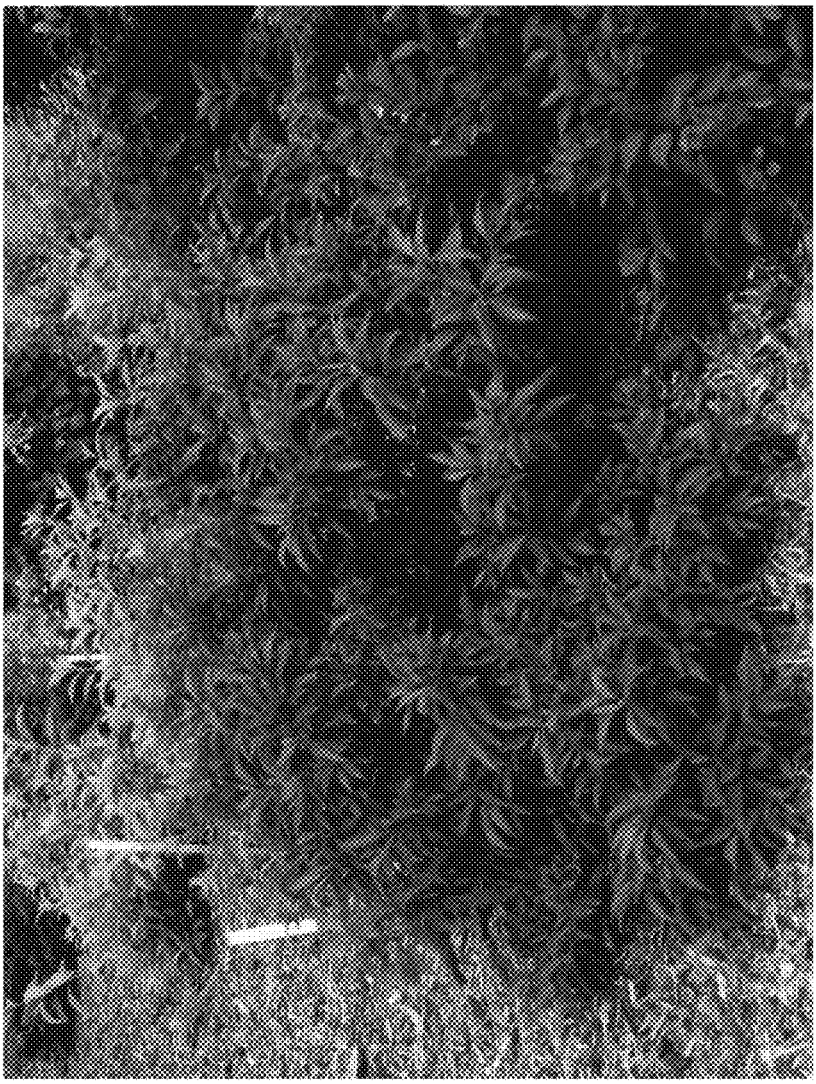
FIG. 2 illustrates a non-flowering plant.
Figure 3:
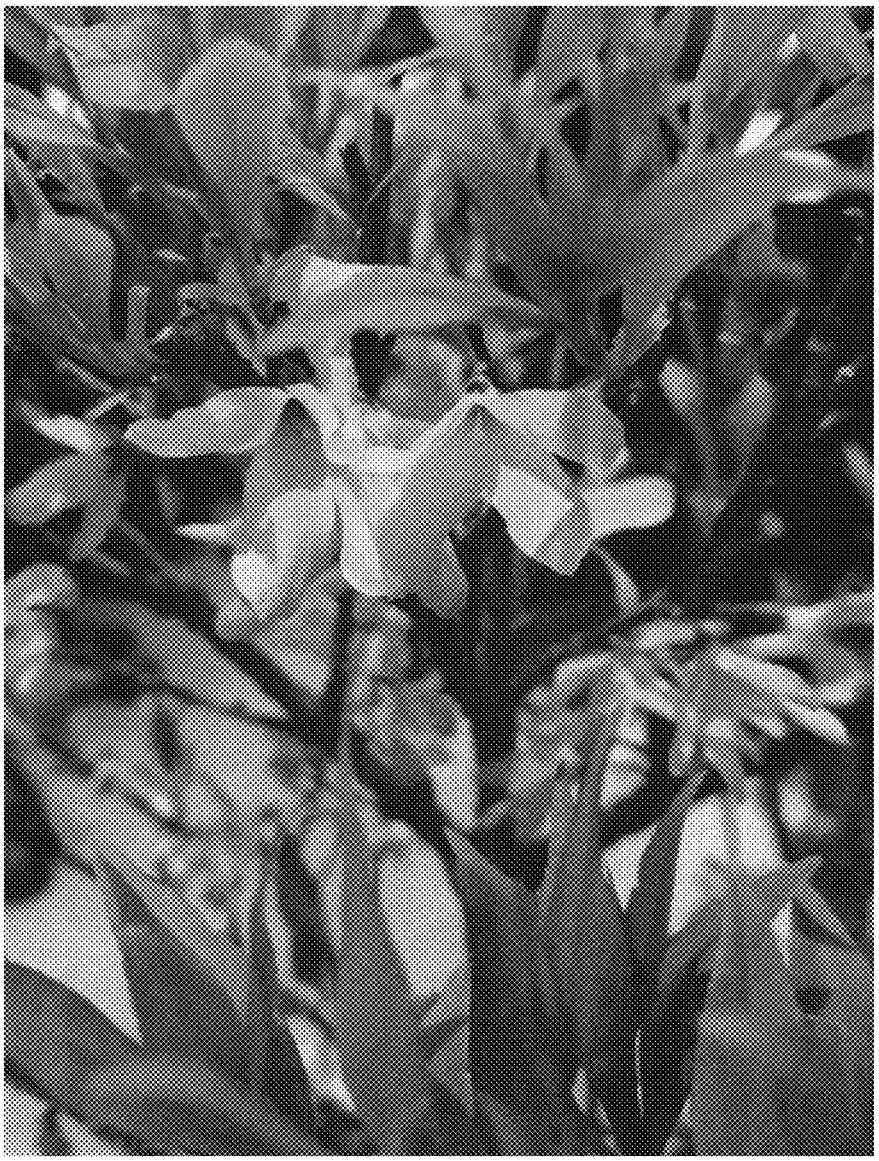
FIG. 3 illustrates a close up view of flowers and foliage. Age of the plant photographed is approximately 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMFXGP' plants grown in a poly-house in Grand Haven, Mich. Measurements were taken during Spring 2017. The plants were 2 years old. The growing temperature ranged from approximately 5° C. to 27° C. Measurements and numerical values represent averages of typical plant types.

Botanical classification: *Forsythia hybrida* 'SMFXGP'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.
Age of plant described: Approximately 2 years old.
Growth habit: Upward and outward.
Pot size of plant described: #1, #2, #3, #5 containers.
Overall plant shape: Mounded.
Height: 46 cm.
Plant spread: 58 cm.
Growth rate: Moderate.
Plant vigor: Vigorous.
Branching habit: Upright and outward.
Length of primary lateral branches: 18 cm.
Diameter of lateral branches: 1 cm.
Quantity of lateral branches: About 20.
Stem:
- *Stem appearance*.—Round.
- *Stem strength*.—Moderate.
- *Aspect*.—0 to 45°.
- *Color*.—RHS Green 138A.
- *Pubescence*.—None.

Internode length: 1 cm.

FOLIAGE

Leaf:
- *Arrangement*.—Opposite, single.
- *Leaf shape*.—Narrowly elliptic.
- *Average length*.—6 cm.
- *Average width*.—1.7 cm.
- *Apex*.—Acute.
- *Base*.—Attenuate.
- *Margin*.—Half entire, half serrulate.
- *Texture of top surface*.—Soft.
- *Texture of bottom surface*.—Smooth.
- *Color*.—Young foliage upper side: RHS Yellow-Green N144C. Young foliage under side: RHS Yellow-Green N144C. Mature foliage upper side: RHS Green 143A. Mature foliage under side: RHS Green 143B.
- *Venation*.—Pattern: Pinnate. Color upper side: RHS Yellow-Green N144B. Color under side: RHS Yellow-Green N144D.
- *Petiole*.—Length: 1 cm. Diameter: 1.5 cm. Petiole color upper side: RHS Green 143A. Petiole color lower side: RHS Yellow-Green N144D. Petiole Texture, upper and under sides: Smooth.

FLOWER

Natural flowering season: April.
Inflorescence type and habit: Spike.
Inflorescence height: 18 cm.
Inflorescence width: 8 cm.
Quantity of flowers per inflorescence: Over 100.
Individual flowers:
- *Flower shape*.—Rotate.
- *Flower aspect*.—Outward.
- *Flowering arrangement*.—Whorled.
- *Length*.—3.5 cm.
- *Height*.—1.5 cm.
- *Persistent or self-cleaning*.—Self-cleaning.
- *Fragrance*.—Lightly earthy.

Bud:
- *Shape*.—Oblong.
- *Length*.—4.1 mm.
- *Diameter*.—3 mm.
- *Color*.—RHS Yellow-Green 146B.

Petal:
- *Petal arrangement*.—Cruciform.
- *Number of petals per flower*.—4.
- *Petal shape*.—Oblong.
- *Petal base*.—Obtuse.
- *Margin*.—Entire.
- *Tip shape*.—Obtuse or retuse.
- *Length*.—2.2 cm.
- *Width*.—6 mm.
- *Texture*.—Upper: Smooth. Lower: Smooth.
- *Color*.—When opening: Upper side: RHS Yellow 9B. Under side: RHS Yellow 9B. Fully open: Upper side: RHS Yellow 9B. Under side: RHS Yellow 9B.

Sepal:
- *Arrangement*.—Cruciform.
- *Appearance*.—Round.
- *Number*.—4.
- *Shape*.—Linear.
- *Tip*.—Cupsidate.
- *Base*.—Truncate.
- *Margin*.—Entire.
- *Length*.—5 mm.
- *Width*.—2 mm.
- *Texture, upper*.—Smooth.
- *Texture, lower*.—Smooth.
- *Color*.—Upper surface at maturity: RHS Yellow-Green 144A, tip Red 46A. Under surface at maturity: RHS Yellow-Green 144A, tip Red 46A.

Calyx:
- *Shape*.—Cruciform.
- *Length*.—1 cm.
- *Diameter*.—1 cm.

Peduncle:
- *Length*.—5 mm.
- *Diameter*.—1 mm.
- *Color*.—RHS Yellow-Green 144A.
- *Angle*.—45-90 degrees.

*Strength*.—Weak-moderate.
*Texture*.—Smooth.
Pedicel: None.

REPRODUCTIVE ORGANS

Stamens:
*Number*.—2.
*Filament length*.—2 mm.
*Filament color*.—RHS Green-Yellow 1C.
Anthers:
*Shape*.—Oval.
*Length*.—2 mm.
*Color*.—RHS Yellow-Orange 17C.
*Pollen color*.—RHS Yellow-Orange 17C.
*Pollen amount*.—Moderate.
Pistil:
*Number*.—2 per flower.
*Length*.—5 mm.
*Style*.—Length: 3.5 cm. Color: RHS Green-Yellow 1C. Ovary Color: RHS Green-Yellow 1C.
Stigma:
*Color*.—RHS Green-Yellow 1C.
*Shape*.—Globular.

OTHER CHARACTERISTICS

Seeds and fruits: Not observed to set fruit and seeds.
Disease/pest resistance: Neither resistance nor susceptibility to normal diseases and pests of *Forsythia* have been observed, aside from mildew resistance.
Temperature tolerance: The new variety tolerates temperatures between −31° C. to 38° C.
Environmental stressors: Good tolerance to wind and rain.

What is claimed is:

1. A new and distinct cultivar of *Forsythia hybrida* plant named 'SMFXGP' as herein illustrated and described.

* * * * *